United States Patent [19]
McMullen

[11] Patent Number: 5,153,002
[45] Date of Patent: Oct. 6, 1992

[54] BIOCOMPATIBLE GRADIENT CONTROLLED RELEASE IMPLANT

[75] Inventor: Jean N. McMullen, Montreal, Canada

[73] Assignee: University of Montreal, Montreal, Canada

[21] Appl. No.: 749,293

[22] Filed: Aug. 23, 1991

Related U.S. Application Data

[63] Continuation-in-part of Ser. No. 663,390, Mar. 4, 1991, abandoned.

[51] Int. Cl.$^5$ .................. A61K 9/26; A61K 9/32; A61K 47/32
[52] U.S. Cl. ................... 424/473; 424/469; 424/470; 424/472; 424/486; 424/482; 424/489; 424/424; 424/425; 424/426; 514/772.3; 514/772.4; 514/772.5; 514/772.6
[58] Field of Search ............. 424/473, 472, 469, 470, 424/486; 514/772.3

[56] References Cited

U.S. PATENT DOCUMENTS

| | | | |
|---|---|---|---|
| 2,987,445 | 6/1961 | Levesque | 424/489 |
| 3,087,860 | 4/1963 | Endicott | 424/469 |
| 3,670,065 | 6/1972 | Eriksson et al. | 424/470 |
| 3,773,919 | 11/1973 | Boswell et al. | 424/19 |
| 4,148,871 | 4/1979 | Pitt et al. | 424/19 |
| 4,341,759 | 7/1982 | Bogentoft et al. | 424/21 |
| 4,419,340 | 6/1983 | Yolles | 424/78 |
| 4,774,091 | 9/1988 | Yamahira et al. | 424/426 |
| 4,793,997 | 12/1988 | Drake et al. | 424/426 |
| 4,897,268 | 1/1990 | Tice et al. | 424/426 |

FOREIGN PATENT DOCUMENTS 0297650 1/1989 European Pat. Off. .

Primary Examiner—Thurman K. Page
Assistant Examiner—E. J. Webman
Attorney, Agent, or Firm—Joseph Scafetta, Jr.

[57] ABSTRACT

A biocompatible and/or biodegradable implant for the substantially constant release, by diffusion, of a therapeutic agent in the outside medium at the site of implant which comprises a body consisting of a core defining a solid mass having walls and being formed of a first biocompatible and/or biodegradable polymeric material and having embedded therein a plurality of solid particles of a therapeutic agent which allows for the diffusion of the therapeutic agent from the core in the outside medium; and a coating of a second biocompatible and/or biodegradable polymeric material which prevents the diffusion of the therapeutic agent in the outside medium and the coating covering all but one of the walls. When diodegradable polymers are used, the degradation half-life of the first and second polymeric materials is longer than the diffusion half-life of the therapeutic agent. The plurality of solid particles of therapeutic agent having varying dimensions, the sizes of which increase from one surface of the core facing the diffusion medium to an opposite wall thus defining a mixture having a concentration gradient; this allows a diffusion of the therapeutic agent at a substantially constant rate. The implant is particularly useful for the slow release of a therapeutic agent in a body fluid.

5 Claims, 2 Drawing Sheets

BIOCOMPATIBLE GRADIENT CONTROLLED RELEASE IMPLANT

RELATED APPLICATION

This application is a continuation-in-part of U.S. application Ser. No. 07/663,390, filed on Mar. 4, 1991.

FIELD OF THE INVENTION

The present invention pertains to a device for the controlled release, by diffusion, of a therapeutic agent.

More particularly, the present invention pertains to a device wherein the diffusion of the therapeutic agent from a supporting element to the outside medium is controlled to maintain a substantially constant rate.

BACKGROUND OF THE INVENTION

Pharmaceutical forms in which medication is delivered at a slow rate may be found in a plurality of polymer-based systems which enable optimization of their effects. Among these systems, some are constituted by a polymeric matrix in which a medication is dispersed in a solid state. When the matrix is subject to dissolution, the medication is gradually released in accordance with a kinetic effect which is characterized by a gradual decrease of the delivery rate. In order to maintain a system which is well adapted to the needs of a patient, it is convenient to modify the rate in a manner that medication is delivered at a constant speed: this is called a "zero-order" delivery rate.

Systems which operate by diffusion are known. In some systems, called reservoirs, diffusion through a membrane is the limiting factor in the delivery process. These systems provide a constant delivery rate if the concentration inside the membrane does not change. In other systems, called matrices, the medication in solid state is dispersed uniformly in a polymeric material. These matrices are said to be non-porous when the medication diffuses through the polymer, in which case the kinetic effect is largely dependent upon the properties of the polymer and the medication concentration. Such systems are said to be homogeneous or heterogeneous whether the solution is in a dissolved state or in a solid state. A porous matrix is also a mean of obtaining a slow release using polymers. The medication is dispersed in solid state or in solution in the pores of the matrix and diffusion to the outside is accomplished through the pores. In these cases, the polymer acts as a carrier and does not interfere with the delivery process.

Matrix forms offer various advantages, one of which is the low possibility of a sudden delivery in the case of damage to the matrix. Also, at the initial stage of dissolution, there is a decrease in latency time and/or in high delivery rate (burst effect). Other advantages are a higher mechanical resistance and a more economical manufacturing method. In the case of porous matrices, the presence of pores enables the delivery of large molecules within a reasonable time; this is particularly useful in the cases of polypeptides.

In recent years, various different approaches have been developed in order to modify the kinetics of delivery of porous matrices with a view to reaching a zero-order delivery rate.

The most common approach consists in modifying the geometry of the system. Since the dissolution of the medication entails a gradual increase of the diffusion path, this can be compensated by a well defined geometry which consists in having a dissolution surface which increases with time. Thus, the quantity of medication being released increases gradually.

OBJECTS AND STATEMENT OF THE INVENTION

It is, therefore, an object of the present invention to provide a device for the controlled release, by diffusion, of a therapeutic agent at a substantially constant rate. This is achieved by compensating the increase of the diffusion path by gradually increasing the active concentration starting from the delivery surface of the matrix.

One object of the present invention, therefore, is the creation of a concentration gradient, by sedimentation of granules of a therapeutic agent in a polymer material.

It has been found that sedimentation of granules, having varying sizes, can provide a gradient in a mixture since they deposit at different speeds. Thus, after solidification of the medium, a matrix with a concentration gradient is obtained.

Sedimentation is defined by the deposit of particles in a fluid under the effect of a force. Gravity force is, of course, a well known deposit method; however, sedimentation can also be obtained by centrifugal force.

An object of the present invention consists in providing a device of the type described above wherein the settling of granules of therapeutic agent in a polymeric material is achieved by centrifugation causing the granules to sediment in a medium by accumulating at the bottom of the recipient where they pack. This packing can be extremely useful when an additional force, such as a centrifugal force, for example, accelerates the deposition of granules.

The present invention relates to a biocompatible and/or biodegradable implant for the substantially constant release, by diffusion, of a therapeutic agent in the outside medium at the site of implant which comprises a body consisting of:

a core defining a solid mass having walls and being formed of a first biocompatible and/or biodegradable polymeric material, the core having embedded therein a plurality of granules of a therapeutic agent and the core allows for the diffusion of the therapeutic agent in the outside medium; and a coating of a second biocompatible and/or biodegradable polymeric material which prevents the diffusion of the therapeutic agent in the outside medium and the coating covering all but one of the walls; wherein the degradation half-life of the first and second polymeric materials is longer than the diffusion half-life of the therapeutic agent when biodegradable polymers are used; and wherein the size of the granules of therapeutic agent increases from the one uncovered wall to an opposite wall thereof thus providing, in the core, a concentration gradient allowing the diffusion of the therapeutic agent from the uncovered wall at a substantially constant rate.

In one preferred form of the invention, the mass is cylindrical with one end surface of the cylindrical body being exposed to diffusion fluids.

Hence, the present invention relates to a novel device in connection with the delivery of therapeutic agents to bring about a desired biological effect, especially when applied subcutaneously to living organisms, such as human beings and particularly animals, such as farm and domestic animals.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

DESCRIPTION OF PREFERRED EMBODIMENT

Figure 1:
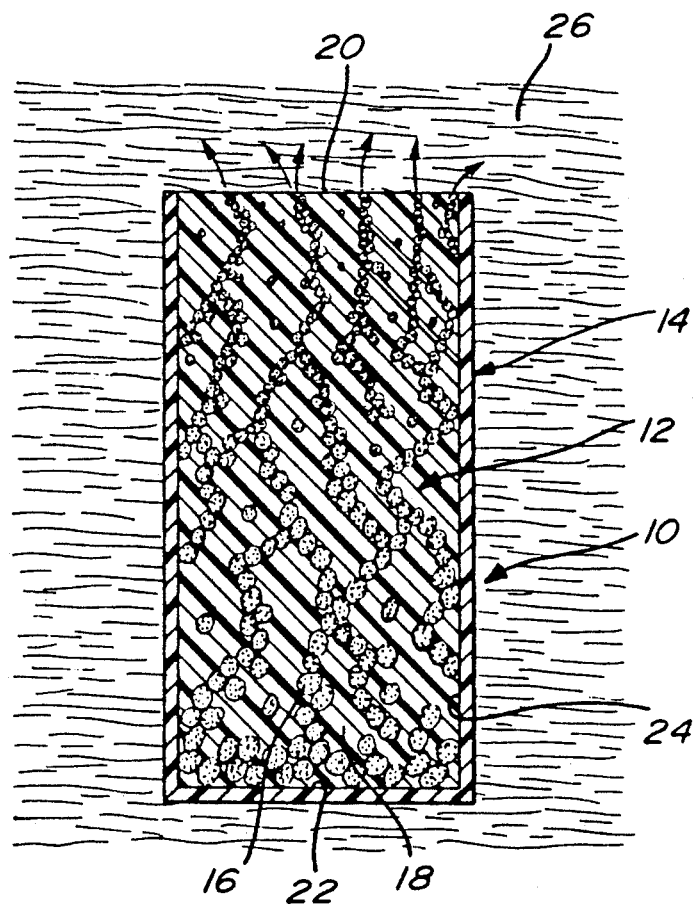
FIG. 1 is a cross-sectional view of one embodiment of a device made in accordance with the present invention.

FIG. 1 shows a device 10 made in accordance with the present invention which comprises a body formed of a core, or matrix, 12 and a coating 14. A desired therapeutic agent previously granulated is embedded by sedimentation into the core 12. The core 12 is made of a polymeric material 18 which is biocompatible and/or biodegradable.

The polymeric material 18 which may be used in accordance with the present invention presents the following advantages:

- Inert in aqueous solution to prevent inflation of the matrix; such characteristic is suitable for porous heterogeneous matrix;
- Biocompatible to prevent use of immunosuppressive agent and to ensure that the immune system will not react with the implant;
- Biodegradable after such a time that the diffusion of the therapeutic agent to the outside of the implant is completed and enables the elimination of the implant from the patient's body only when the implant is depleted from the drug;
- Stable and rigid at room temperature to ensure a constant form and to prevent crumbling during the cutting; and
- the polymeric material is malleable and has a melting point or controlled polymerization that enables the sedimentation of the therapeutic agent therein, and for which it has to be liquid or at least semi-solid.

Polymeric materials which can be used for the core in accordance with the present invention may be selected from the list below:

Poly-ε-caprolactone
Polyethylene
Ethylvinyl acetate copolymer (EVAC)
Polylactic acid
Silicone rubber
Polymethyl methacrylate The suitable polymeric material is chosen depending on its biocompatibility and/or its half-life of degradation and the therapeutic agent to be delivered. The degradation half-life of the polymeric material must be longer than the time required for the total diffusion of the therapeutic agent.

The therapeutic agent used in accordance with the present invention may be any desired therapeutic agent, hormones, enzymes, and the like, such as heparin, morphine, estradiol, growth releasing factor (GRF) and gonadotropin releasing hormone (GMRH).

The therapeutic agent must be in granulated form.

For the purpose of the present invention, poly-(ε-caprolactone) is preferred for various reasons. It is a totally inert material in an aqueous medium; it does not swell thereby being convenient for heterogeneous porous matrices. It is a biocompatible and biodegradable polymer and its half-life of degradation is about 230 days.

In order to carry out the sedimentation of the therapeutic agent in the polymeric material, the latter must be in a liquid state, or at least semi-solid. The melting point and the malleability of the polymer, thus, are important points to be considered; the poly(ε-caprolactone) responds to these criteria. Its rigidity at room temperature is such that it maintains its shape without becoming brittle when being cut. Near its melting point, it is very viscous; it must be further heated in order to allow the sedimentation of the therapeutic agent.

Similarly, the coating 14 is formed of a biocompatible material which may be a polymer similar to the polymeric material 18 provided that is impermeable to water and to the granules of therapeutic agent.

Polymeric materials which can be used for the coating in accordance with the present invention may be selected from the list below:

Poly-ε-caprolactone
Polyethylene
Ethylvinyl acetate copolymer (EVAC)
Polylactic acid
Silicone rubber
Polymethyl methacrylate In the preferred embodiment illustrated, the mass of the matrix 12 has a cylindrical shape with opposite end walls 20 and 22 and side wall 24. This shape can be explain by the use of a cylindrical tube for the centrifugation such as a test tube. Other shapes may also be used.

It is to be noted that the size of the granules 16 increases from the surface 20 to the opposite wall 22. In accordance with Stokes law, the granules sediment at a rate which is proportional to their size. Therefore, after centrifugation, there is formed a sediment of a well defined configuration which is a function of the size distribution of the initial powder. Therefore, the base of the sediment is generally constituted of larger granules while the smaller particles are situated adjacent the surface 20. The large granules have a much smaller surface-to-volume ratio; hence, there is a larger concentration of therapeutic agent at the bottom 22 than at the surface 20.

A coating covers the walls of the cylindrical mass except on surface 20. The uncovered surface is in contact with the dissolution medium 26 which when used in situ is the blood, plasma or any other biological fluids. The arrangement of granules of the therapeutic agent in the matrix 12 defines a concentration gradient to achieve, as close as possible, a constant zero-order delivery rate from surface 20.

Figure 2:
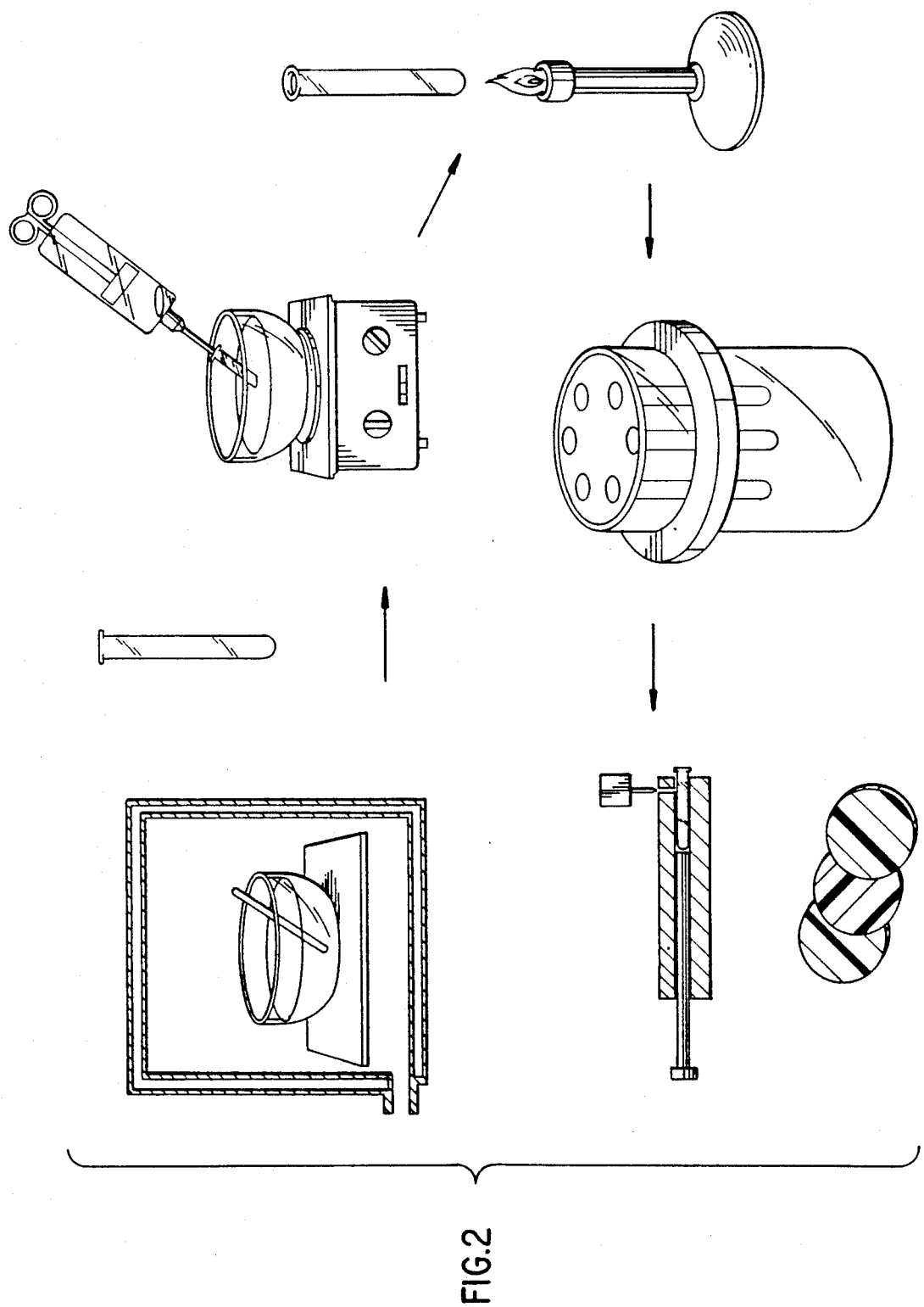
FIG. 2 show one embodiment of the production of a matrix in accordance with the present invention.

The construction of the core 12 is accomplished in five steps. First, the polymeric material is purified. Second, the melted purified polymeric material is mixed with a therapeutic agent and placed in vacuo to remove air bubbles in the material. The melted polymeric material is then introduced into a cylindrical plastic test tube by means of a syringe that pierces through the extremity of the tube at the opposite end of its upper opening. The test tube still having the syringe fixedly attached is turned upside down to introduce its opening into the melted polymeric material. By removing the air from the tube with the syringe, a vacuum is created forcing the polymeric material through the upper opening of the tube (FIG. 2).

This technique is used to assure a rapid and uniform filling of the test tube. Third, the syringe is pulled out of the extremity of the test tube, and the hole created by the syringe is sealed under a flame. Fourth, the test tube containing the polymeric material is placed in the centrifuge (sold by Intl. Equipment Co., Boston Ma) for sedimentation. To assure a constant temperature of the polymeric material, the centrifuge is placed in an oven at a desired temperature. Finally, after the completion of the sedimentation, the test tube is cut with a single cutting edge blade to obtain a matrix 12 of a desired thickness. The matrix is then removed from the part of the test tube still surrounding the matrix.

The coating surrounding the matrix is chosen as a function of the desired therapeutic agent. The polymeric material will have to be impermeable to such a point that the dissolution medium and the therapeutic agent will not to diffuse through the coating. As far as the matrix is concerned, the coating must be biocompatible to prevent any rejection by the organism or the need of an immunosuppressive agent. The coating will also have to be biodegradable to prevent subsequent removal of the implant once depleted of its therapeutic agent dosage. However, the biodegradability must be such that its half-life will be longer than the time of the complete diffusion of the therapeutic agent to ensure the effect of the gradient of concentration. The coating will be applied on the matrix according to the procedure well known depending on the polymeric material used for the coating.

During matrix dissolution, the porosity created by the liberation of the therapeutic agent from the polymeric material increases as the dissolution front penetrates into the matrix. It has also been found that a gradual increase in the size of granules results in a gradual decrease of the local tortuosity thereby providing an additional compensation effect for the increasing diffusion distance.

The present invention will be more readily understood by referring to the following examples which are given to illustrate the invention rather that to limit its scope.

EXAMPLE I

For the purpose of Example I, sodium salicylate was selected as the therapeutic agent. This medication has been chosen for various reasons. First, this agent is extremely soluble in an aqueous medium which is a condition that enables one skilled in the art to neglect the effect on solubility that the low concentration of medication could have on the diffusion of the therapeutic agent in the outside medium. The sodium salicylate is also characterized by its granulometry which consists of different sizes of granules between 5 and 180 $\mu$m. This characteristic is an important factor for the study of the gradient, because extremely variable size distributions can be obtained. Finally, sodium salicylate has also the advantage of being easily measured with a spectrophotometer and is extremely resistant to heat and light.

The polymer chosen for this experiment was poly($\epsilon$-caprolactone). the polymer was first purified by precipitation in methanol. The polymeric material is dissolved in a sufficient amount of dichloromethane, and that solution is added to a solution of methanol in a ratio of 1:4 v/v. The resulting mixture is stirred until all the polymeric material is precipitated. The supernatant is removed from the partly pruified polymer, and the procedure is repeated once more. The purified poly($\epsilon$-caprolactone is subsequently dried in an oven for 12 hours.

A mixture of the purified poly($\epsilon$-caprolactone) and 30% p/o of sodium salicylate is heated at 105° C. for one hour under vacuum, after which time the mixture is stirred and heated again at the same temperature for another hour under vacuum, to ensure that all air bubbles are removed therefrom.

A mixture of the purified poly($\epsilon$-caprolactone) and 30% p/p of sodium salicylate was placed under vacuum conditions in an oven at 105° C. for one (1) hour. The mixture was then remixed and replaced in a vacuum oven to ensure that it was free of air bubbles.

The mixture is placed in a cylindrical tube for centrifugation. The test tube is made of polypropylene (Sarstedt®, sold by St-Laurent, #72-702 400 $\mu$l) with a length of 45 mm. This test tube was chosen because it is easy to place in the centrifuge, has good resistance at the temperature of filling and centrifugation, is rigid enough for an easy cut, and finally the matrix does not stick on the walls of the test tube.

The syringe used to fill the test tube was a 5 ml syringe with a 22G-1 ® needle. The test tube was filled by plunging the opening side of the tube in the compound mixture and by creating a vacuum in the test tube with the syringe installed at the diametrally opposite side of the tube.

The test tube was then placed in the centrifuge at a speed of 11,600 rpm (corresponding to about 10,000 g). The centrifugation temperature was set at 100° C. and the time of centrifugation was ninety (90) minutes. Subsequently, the test tube was pulled out of the centrifuge and cut with a single cutting edge blade at different lengths varying from 14 to 24 mm, to give different lengths of matrix with different concentration gradients.

EXAMPLE II

Proceeding in substantially the same manner as in Example I but varying the time or speed of the centrifugation depending on the desired concentration gradient of the matrix.

EXAMPLE III

Proceeding in substantially the same manner as in Example I but varying the size of granules of the therapeutic agent depending on the desired rate of diffusion.

EXAMPLE IV

Proceeding in substantially the same manner as in Example I but substituting poly($\epsilon$-caprolactone) with another polymeric material and analyzing the matrix to maximize the experimental conditions for obtaining a desired concentration gradient.

Although the invention has been described above with respect with one specific form, it will be evident to a person skilled in the art that it may be modified and refined in various ways. For example, sedimentation has been described above as occurring in a molten polymeric material. However, sedimentation could also occur in a liquid polymer precursor monomer before it polymerizes to a solid. Also, the concentration gradient could be achieved, instead of by sedimentation, by multi-layer sintering of polymer films. A multi-layer sintering of the polymer films is a well known technique which results in welding together polymer films. It is therefore wished to have it understood that the present invention should not be limited in scope, except by the terms of the following claims.

The embodiment of the invention in which an exclusive property or privilege is claimed are defined as follows:

1. A biocompatible and/or biodegradable implant for controlled release, by diffusion, of a therapeutic agent into an outside medium at a site of the implant which comprises a body consisting of:

a core defining a solid mass having walls and being formed of a first biocompatible and/or biodegradable polymeric material, said core having embedded therein a plurality of granules of the therapeutic agent and said core allowing for diffusion of the therapeutic agent into the outside medium; and a coating of a second biocompatible and/or biodegradable polymeric material which prevents the diffusion of the therapeutic agent into the outside medium, said coating covering all but one of the walls of the solid mass;

wherein the degradation half-lifes of the first and the second polymeric materials are longer than diffusion half-life of the therapeutic agent when biodegradable polymers are used; and further wherein the size of the granules increase from the one uncovered wall to an opposite wall thereof, thus providing, in the core, a concentration gradient allowing controlled diffusion of the therapeutic agent from the uncovered wall.

2. A device as defined in claim 1, wherein said polymeric material is poly($\epsilon$-caprolactone).

3. A device as defined i claim 1, wherein said mass is cylindrically shaped and wherein said uncovered wall is one of the two opposite end walls of the cylindrically shaped mass.

4. A method for the production of a biocompatible and/or biodegradable implant, according to claim 1, for controlled release, by diffusion, of a therapeutic agent into an outside medium at a sit of the implant, aid implant including a core defining a solid mass having walls and being formed of a first biocompatible and/or biodegradable polymeric material, said implant also including a coating of a second biocompatible and/or biodegradable polymeric material which prevents diffusion of the therapeutic agent into the outside medium, said method comprising the steps of:

(a) heating a mixture of said therapeutic agent and said first polymeric material to obtain a liquid state or a semi-solid state;

(b) removing air bubbles from the mixture under vacuum;

(c) sedimenting the mixture freed of air bubbles by step (b) in a container to obtain a matrix;

(d) cutting the container and removing the matrix obtained in step (c) to form the core; and (e) covering all but one of said walls of said core with said coating.

5. The method of claim 4, wherein the sedimenting in step (c) is accomplished by centrifuging the mixture freed of air bubbles.

* * * * *